United States Patent [19]

Citterio et al.

[11] Patent Number: 4,845,281

[45] Date of Patent: Jul. 4, 1989

[54] METHOD OF PREPARING KETOPROFEN

[75] Inventors: Attilio Citterio; Daniele Fancelli, both of Milan, Italy

[73] Assignee: Blaschim, S.p.A., Italy

[21] Appl. No.: 226,017

[22] Filed: Jul. 29, 1988

[30] Foreign Application Priority Data

Aug. 6, 1987 [IT] Italy .............................. 21594 A/87

[51] Int. Cl.$^4$ .............................................. C07C 59/76
[52] U.S. Cl. .................................... 562/460; 548/486; 562/433; 562/491
[58] Field of Search ........................................ 582/460

[56] References Cited

U.S. PATENT DOCUMENTS

| | | | |
|---|---|---|---|
| 1,711,164 | 4/1929 | Adams | 562/460 |
| 3,621,037 | 11/1971 | Thials et al. | 562/460 |
| 4,058,559 | 11/1977 | Jones | 562/460 |
| 4,695,648 | 9/1982 | Aghack | 562/460 |
| 4,714,776 | 12/1982 | Bell | 562/460 |

Primary Examiner—Paul J. Killos
Attorney, Agent, or Firm—Berman, Aisenberg & Platt

[57] ABSTRACT

A method of preparing ketoprofen by reacting aniline with a halide of an alpha-halogen propionic acid, benzylation of 3-methyl-2-indolinone, alkaline hydrolysis of 5-benzyl-3-methyl-2-indolinone, deamination of 2-(3-benzyl-6-aminophenyl)propionic acid and oxidation of 2-(3-benzylphenyl)propionic acid.

12 Claims, No Drawings

METHOD OF PREPARING KETOPROFEN

The invention relates to a method of preparing ketoprofen.

Ketroprofen [chemical name 2-(3-benzoylphenyl)-propionic acid] is a known anti-inflammatory drug.

British Pat. No. 1 164 855 describes a method of preparing ketoprofen by oxidation of 2-(3-benzylphenyl) propionic cid. The latter substance, however, is prepared by a very complex process comprising the following steps:

preparation of 2-(4-aminophenyl)propionic acid according to F. Nerdel et al. (Ber 87, 217, 1954);

diazotation of 2-(4-aminophenyl)propionic acid and subsequent reaction of diazonium salt with potassium xanthogenate to give 2-(4-thiophenyl)-propionic acid;

reaction of 2-(4-thiophenyl)propionic acid with 2-iodobenzoic acid to give 2-[4-(2-carboxyphenylthio)-phenyl]-propionic acid;

heating the latter substance with polyphophoric acid to give 2-(2-thiaxanthonyl)-propionic acid, and treatment of 2-(2-thiaxanthonyl)propionic acid with Raney nickel to give 2-(3-benzylphenyl)-propionic acid.

This process is certainly unsuitable for operation on an industrial level owing to the extremely low yields and the large amount on labour required.

It has now been found that 2-(3-benzyl)propionic acid can be prepared with much higher yields and with considerable saving of labour by the following method of synthesis:

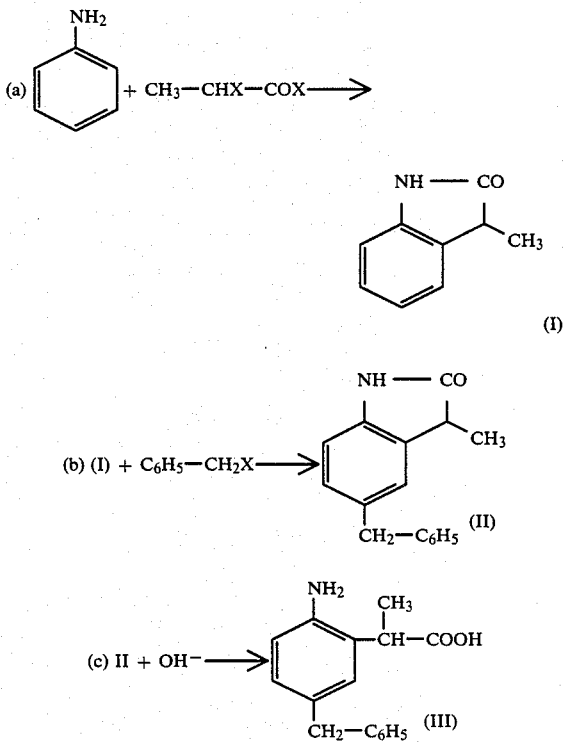

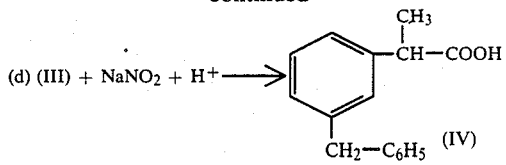

where X is a chlorine or bromine.

The invention therefore relates to a method of preparing ketoprofen comprising:

(a) reacting aniline with a reactive derivative of an alphahalogen-propionic acid according to Stollë;

(b) benzylation of the resulting 3-methyl-2-indolinone with a benzyl halide according to Friedel-Crafts;

(c) alkaline hydrolysis of the resulting 5-benzyl-3-methyl-2-indolinone;

(d) replacement of the amino group in 2-(3-benzyl-6-aminophenyl)propionic acid with a hydrogen atom, and (e) oxidation of 2-(3-benzylphenyl)propionic acid.

Phase (a) is carried out by first reacting aniline with a reactive derivative of an alpha-halogen-propionic acid (preferably at a temperature between $-20°$ C. and $110°$ C. and in the presence of a suitable organic diluent) and, after formation of the alpha-halogen propionanilide, in the presence of a Lewis acid at $100°-200°$ C. The second part is preferably carried out in the absence of organic diluents. Examples of suitable reactive derivatives of alpha-halogen propionic acid are anhydride, chloride and bromide. When the reactive derivative is an acid halide, the first part of step (a) is preferably carried out in the presence of a suitable organic or inorganic base capable of capturing the hydrohalic acid formed. Examples of suitable bases are alkali-metal and alkaline earth carbonate and bicarbonate and tertiary amines, such as trimethylamine, pyridine or an excess of the aniline itself. Examples of suitable organic diluents are ethyl ether, dioxane, methylene chloride and toluene. Examples of suitable Lewis acids are $AlCl_3$, $BCl_3$ and $SbCl_5$.

Step (b) is carried out in the presence of a suitable Friedel Crafts catalyst, such as aluminium chloride. The reaction is preferably carried out at a temperature between $-10°$ C. and the reflux temperature or melting point of the reaction mixture. When a diluent is used, it may conveniently be chosen from the diluents suitable for the Friedel Crafts reaction, eg. aliphatic hydrocarbons or chlorinated aromatics or nitrobenzene or carbon disulphide or the like.

After step (c), which is carried out in conventional manner, step (d) is carried out by an unusual manner, by dissolving the amine of formula III and an alkali-metal nitrite in an aqueous solution of an alkali-metal hydroxide. The resulting solution is added dropwise to an aqueous solution of a mineral acid and hypophosphorous acid is finally added. This rather unusual method of operation is justified by the fact that in the particular case of the formula III amine, it is impossible to use the method of deamination in an acid medium since, at acid pH, the substance is immediately converted to indolinone II which is unresponsive to deamination.

The reaction between the alkaline solution and the mineral acid solution is preferably carried out at a temperature between $-15°$ C. and $0°$ C. Preferably hypophosphorous acid is added to the mixture obtained after adding the alkaline solution dropwise to the solution of mineral acid, but alternatively hydrophosphorous acid can be added to the mineral acid solution before adding the alkaline solution dropwise.

Preferably from 1.05 to 1.2 mols of alkali-metal nitrite and 2.5 mols of hypophosphorous acid are added per mol of amine of formula III.

An organic solvent in which the formula III amine and/or the formula IV compound is soluble can be added to the aqueous solution of mineral acid.

Examples of solvents of the first kind are: low molecular-weight aliphatic alcohols such as methanol and isopropanol; cyclic ethers, such as tetrahydrofuran and dioxane; and low molecular-weight amides such as dimethyl formamide. Examples of solvents of the second kind are: chlorinated aliphatic hydrocarbons, such as methylene choride, chloroform and 1,2-dichloroethane; aromatic hydrocarbons, such as toluene and xylene, cyclic aliphatic hydrocarbons, such as cyclohexane; and mixtures thereof.

After hypophosphorous acid has been added, the reaction time can be reduced by adding a suitable catalyst, such as powdered copper, cuprous oxide or coprous salts.

The amount of catalyst is preferably from 1 to 3% by weight of the amine which is reacted. The reaction is then brought to completion by letting the temperature rise to ambient temperature.

Finally step (e) can be carried out by conventional methods for converting a methylene group into a carbonyl group, e.g. oxidation with potassium permanganate in the presence of hot sulphuric acid, preferably at the boiling-point of the reaction mixture.

The skilled addressee will immediately note that the method of synthesising ketoprofen according to the invention is based on a synthesis process involving an original combination of a number of known techniques such that, as a whole, it represents an appreciable technical advance in the synthesis of ketoprofen via oxidation of compound IV.

The following examples illustrate the invention without limiting it.

EXAMPLE 1

3-methyl-2-indolinone (I)

(a) Alpha-chloropropionyl chloride (132.3 g; 1.05 mols) in ethyl ether (200 ml) and triethylamine (107 g; 105 mols) in ethyl ether (200 ml) were simultaneously added dropwise to a solution of aniline (91 g; 1 mol) in ethyl ether (200 ml) kept at 15°–20° C. with agitation. After an hour the solvent was evaporated.

(b) Aluminium trichloride was added to the previously obtained solid residue, and the mixture was gradually heated with agitation. After completely melting, the mixture was heated to 150° C. for 4 hours, removing the hydrochloric acid which formed. The mixture was slowly cooled to 70° C. and then poured into a mixture of chloroform (250 ml), ice (100 g) and concentrated hydrochloric acid (100 ml).

The aqueous phase was separated, brought to pH 4 with sodium carbonate and extracted with chloroform (3×20 ml). The combined organic extracts are washed with water, dehydrated and concentrated.

The residue was distilled in vacuo (1 ml Hg) and the fraction boiling at 125°–130° C. was collected. It was dissolved in hot methanol (200 ml), then water was added (62 ml). The mixture was left to stand at 15° C. overnight. 88 g of a straw-coloured crystalline product melting at 122°–123° C. were obtained by filtration.

Another 9 g of the desired product were recovered from the mother liquors.

EXAMPLE 2

5-benzyl-3-methyl-2-indolinone (II)

The reaction mixture in the preceding example was slowly cooled to 30° C. After adding methylene chloride (210 ml), the mixture was cooled to −10° C.

Benzyl chloride (13.7 g; 0.11 mols) was added to the mixture, keeping the temperature at −10° C. At the end of the addition process, the reaction mixture was kept under agitation at the same temperature. After an hour the temperature was allowed to rise to 20° C., and the mixture was kept under agitation at this temperature for four hours.

The reaction mixture was then slowly added dropwise to a solution (100 ml) of 10% hydrochloric acid kept at 0° C. The organic phase was washed with water, dried on sodium sulphate and evaporated at reduced pressure.

The residue was dissolved in hot methyl alcohol (50 ml), and the solution was slowly cooled to 0° C. The crystalline precipitate was separated by filtration and dried in an oven in vacuo.

The product was compound II (10.9 g; m.p. 128°–129° C.)

EXAMPLE 3

2-(3-benzylphenyl)propionic acid (IV)

Compound II (10 g; 0.042 mols) was suspended in 3N sodium hydroxide under nitrogen, and the obtained suspension was refluxed with agitation for 10 hours, also under nitrogen. The solution was filtered and cooled to 0° C.

A solution of sodium nitrite (3.5 g; 0.05 mols) in water (50 ml) was added to the first solution.

The resulting solution was added to a solution (100 ml) of 20% hydrochloric acid kept at −5° C. to −7° C. under agitation. At the end of the addition process, 50% hypophosphorous acid (13.8 g; 0.126 mols) was added, the mixture still being kept at about −5° C. and under agitation. It was then left to warm up to ambient temperature and agitation was continued overnight. The reaction mixture was then extracted with ethyl ether (3×70ml); the organic phase was washed with water and extracted with 10% sodium hydroxide. The aqueous solution was separated and acidified with concentrated hydrochloric acid or glacial acetic acid.

The resulting oil was dissolved in ethyl ether (5 ml), cooled to 0° C. and treated with pentane (30 ml).

The crystalline precipitate was separated by filtration and dried in an oven in vacuo.

The product was compound IV (6.5 g; m.p. 120° C.).

EXAMPLE 4

2-(3-benzoylphenyl)propionic acid (ketoprofen)

Compound IV (4.8 g; 0.02 mols) was suspended in a solution of potassium permanganate (3.2 g; 0.02 mols) in distilled water (100 ml) containing concentrated sulphuric acid (4 ml). The mixture was refluxed for 6 hours, then cooled to ambient temperature and decanted. The organic phase was separated and extracted with 1N sodium hydroxide and the aqueous phase was separated and acidified with concentrated hydrochloric acid at a temperature below 10° C. The thus-separated solid was dried in vacuo at 40° C. for 5 hours and then crystallised from 1:2 isopropyl ether:pentane.

The product was ketoprofen (2.5 g, m.p. 92°–93° C.).

We claim:

1. A method of preparing ketoprofen by (a) reacting aniline with a reactive derivative of an alpha-halogen propionic acid, (b) benzylation of the resulting 3-methyl-2-indolinone with a benzyl halide; (c) alkaline hydrolysis of the resulting 5-benzyl-3-methyl-2- indolinone, (d) replacement of the amino group in the resulting 2-(3-benzyl-6-aminophenyl)propionic acid with a hydrogen atom and (e) oxidation of 2-(3-benzylphenyl)-propionic acid.

2. A method according to claim 1, characterised in that step (a) is carried out by first reacting aniline with the anhydride, the chloride or the bromide of the alpha-halogen propionic acid at a temperature between −20° C. and 110° C. and, after formation of the alpha-halogen propionanilides, in the presence of a Lewis acid at 100°–200° C.

3. A method according to claim 2, characterised in that the first part of step (a) is carried out in the presence of an organic diluent chosen from among ethyl ether, dioxane, methylene chloride and toluene and, when a chloride or bromide of the alpha-halogen propionic acid is used, in the presence of also an organic or inorganic base capable of capturing the hydrohalic acid formed.

4. A method according to claim 1, characterised in that step (b) is carried out in the presence of aluminium chloride and at a temperature between −10° C. and the reflux temperature or melting point of the reaction mixture.

5. A method according to claim 4, characterised in that step (b) is carried out in the presence of an organic diluent chosen from among aliphatic hydrocarbons, chlorinated aromatics, nitrobenzene and carbon disulphide.

6. A method according to claim 1, characterised in that step (d) is carried out by dissolving 2-(3-benzyl-6-aminophenyl)propionic acid and an alkali-metal nitrite in a solution of an alkali-metal hydroxide, adding the resulting solution to a mineral acid in solution and finally adding hypophosphorous acid.

7. A method according to claim 6, characterised in that the alkaline solution is reacted with the mineral-acid solution at a temperature between −15° C. and 0° C.

8. A method according to claim 6, characterised in that the alkaline solution is added to a solution containing both the mineral acid and hypophosphorous acid.

9. A method according to claim 6, characterised in that from 1.05 to 1.2 moles of alkali-metal nitrite and from 2 to 5 mols of hypophosphorous acid are added per mol of 2-(3-benzyl-6-aminophenyl)propionic acid.

10. A method according to claim 6, characterised in that the reaction is carried out in the presence of an organic solvent chosen from among low molecular-weight aliphatic alcohols, cyclic ethers, low molecular-weight amides, chlorinated aliphatic hydrocarbons, aromatic hydrocarbons, cyclic aliphatic hydrocarbons and mixtures thereof.

11. A method according to claim 6, characterised in that the reaction with hypophosphorous acid is catalysed by adding a quantity of powdered copper from 1% to 3% by weight of 2-(3-benzyl-6-aminophenyl)propionic acid.

12. A method according to claim 1, characterised in that phase (e) is brought about with potassium permanganate in the presence of hot sulphuric acid.

* * * * *